United States Patent [19]

Abrevaya et al.

[11] Patent Number: 5,414,183
[45] Date of Patent: May 9, 1995

[54] NITROGEN REMOVAL FROM LIGHT HYDROCARBON FEED IN OLEFIN ISOMERIZATION AND ETHERICATION PROCESS

[75] Inventors: Hayim Abrevaya, Wilmette; Suleyman M. Ozmen, Winnetka; Paul T. Barger, Arlington Heights; Christopher D. Gosling, Roselle; Thomas A. Verachtert, Wheeling, all of Ill.

[73] Assignee: UOP, Des Plaines, Ill.

[21] Appl. No.: 996,463

[22] Filed: Dec. 24, 1992

[51] Int. Cl.⁶ .................. C07C 5/27; C07C 41/00; C01G 19/02
[52] U.S. Cl. ..................... 585/671; 585/314; 585/315; 585/664; 208/254 R; 568/697
[58] Field of Search ............... 585/310, 314, 315, 664, 585/666, 671, 259; 568/697; 208/254 R, 228

[56] References Cited

U.S. PATENT DOCUMENTS

| | | | |
|---|---|---|---|
| 3,062,883 | 11/1962 | Gilbert et al. | 260/561 |
| 3,381,034 | 4/1968 | Greene et al. | 260/557 |
| 4,096,149 | 6/1978 | Feldman et al. | 260/295.5 A |
| 4,440,871 | 4/1984 | Lok et al. | 502/214 |
| 4,566,965 | 1/1986 | Olmstead | 208/11 R |
| 4,886,925 | 12/1989 | Harandi | 585/331 |
| 5,120,881 | 6/1992 | Rosenfeld et al. | 568/697 |
| 5,132,484 | 7/1992 | Gajda et al. | 585/667 |
| 5,166,455 | 11/1992 | Chin et al. | 568/697 |

*Primary Examiner*—P. Achutamurthy
*Attorney, Agent, or Firm*—Thomas K. McBride; John F. Spears, Jr.; Richard E. Conser

[57] ABSTRACT

An improved process is disclosed for the removal of nitrogen compounds from light hydrocarbon streams. Such nitrogen removal enhances the performance of catalytic processes which upgrade light hydrocarbons, especially light olefins, such as isomerization and etherification. The nitrogen-removal process can usefully be combined with steps for removal of sulfur compounds and highly unsaturated compounds in a process combination for upgrading the light hydrocarbons.

14 Claims, 5 Drawing Sheets

NITROGEN REMOVAL FROM LIGHT HYDROCARBON FEED IN OLEFIN ISOMERIZATION AND ETHERICATION PROCESS

BACKGROUND OF THE INVENTION

1. Field of the Invention

This invention relates to an improved process for contaminant removal from hydrocarbons, and more specifically for the removal of nitrogen compounds from light hydrocarbons.

2. General Background

Nitrogen removal from petroleum stocks is widely practiced in the refining industry. Combined nitrogen may be undesirable from the standpoint of product quality or because nitrogen in fuels may increase emissions of nitrogen oxides during fuel combustion. Nitrogen removal often is dictated by the sensitivity to nitrogen of catalysts used in downstream processing units to this contaminant. Reforming catalysts usually are deactivated by the amounts of nitrogen found in cracked naphthas, for example, and heavy-oil feedstocks to selective hydrocracking catalysts may need treating for nitrogen reduction. Nitrogen removal from such stocks is effected by catalytic hydrotreating at elevated pressures and temperatures. Catalytic hydrotreating of light hydrocarbons, such as $C_3$, $C_4$, and $C_5$ hydrocarbons, for nitrogen removal generally is not practiced due to high processing costs and concomitant loss of valuable light olefins which often are present in such streams.

Nitrogen compounds may be present in cracked, olefinic light-hydrocarbon streams as a result of the conversion of heavy nitrogen-containing molecules in the cracking feedstocks. Such nitrogen compounds found in these streams are removed to a large extent by water washing as would be practiced in many petroleum refineries. Conventional catalytic processing units which upgrade light olefinic hydrocarbons, such as polymerization and alkylation units, are not significantly affected by any remaining nitrogen.

New processing developments, however, are reducing the acceptable levels of nitrogen in light hydrocarbon streams. There is an increasing need for isobutene, isopentene and other tertiary-carbon olefins as chemical intermediates and for production of methyl t-butyl ether (MTBE), methyl t-amyl ether (TAME) and other ethers as gasoline components. MTBE and TAME in particular are experiencing rapid growth in demand as gasoline components, as restrictions on gasoline olefins and volatility force olefins out of gasoline and as ethers and alcohols are needed for reformulated gasolines with higher oxygen content. The need for branched-chain olefins as ether feedstocks increasingly exceeds the availability, and catalytic isomerization to alter the ratio of olefin isomers is one solution to this need.

Highly active and selective catalysts for olefin isomerization surprisingly have been found to be sensitive even to small quantities of weakly basic nitrogen compounds in the isomerization feed. Thus, nitrogen levels in light hydrocarbon streams that have been acceptable in catalytic processes in the past now must be reduced in order to effect olefin isomerization. Surprisingly in view of their relative boiling points, acetonitrile and propionitrile have been found in harmful quantities in light olefinic streams from FCC units. Conventional water washing and adsorption often do not result in sufficient removal of nitrogen compounds from hydrocarbon streams, and in addition, the nitrogen-containing streams from such removal processes present disposal problems. A problem facing workers in the art therefore is to provide technology to reduce nitrogen contaminants in light hydrocarbon streams below levels previously thought necessary for subsequent catalytic processing.

U.S. Pat. No. 5,191,146 discloses a process for the isomerization of pentenes or butenes using a highly selective non-zeolitic molecular-sieve catalyst, but does not suggest the need to remove nitrogen from the feestock.

The hydrolysis of nitriles to produce amides, and the further reaction of amides to form ammonia and carboxylic acids, are known in the art. U.S. Pat. No. 3,062,883 (Gilbert et al.) teaches a process for hydrolyzing nitriles in the presence of water and in the presence of a strongly basic resin to selectively yield the respective amides; using a styrene divinyl benzene copolymer substituted with tetramethyl ammonium hydroxide moieties as the resin, low temperatures avoid acid formation. U.S. Pat. No. Re. 28,525/3,381,034 (Greene et al.) discloses a process for hydrolyzing a variety of nitriles using a copper salt, which also may contain metallic copper, in the presence of water and optionally several other polar solvents; the products are relatively pure and easily recovered. U.S. Pat. No. 4,096,149 (Feldman et al.) teaches a method for the hydrolysis of a wide range of nitriles utilizing supported rhodium and a thiophosphite, with preferably mildly basic media based on water as the hydrolyzing agent.

Removal of nitrogen from hydrocarbons by adsorption using a zeolite is taught in U.S. Pat. No. 5,120,881 (Rosenfeld et al.) Copending application Ser. No. 08/031,795 teaches a combination for removal of sulfur and polar compounds from a $C_3$–$C_5$ fraction, using adsorption to remove traces of polar compounds. Applicants believe that none of the art anticipates or suggests the invention described hereinbelow, which removes nitrogen compounds directly from light hydrocarbon streams while avoiding problems associated with adsorption processes such as finding a suitable desorbent and conversion or disposal of desorbed nitrogenous contaminants.

SUMMARY OF THE INVENTION

An objective of the invention is to remove nitrogen compounds which could harm catalytic processes from light hydrocarbon streams, particularly from olefin-containing streams which are to be processed by isomerization.

This invention is based on the discovery that nitriles present in a light hydrocarbon stream to an extent which could harm an olefin-isomerization catalyst could be effectively hydrolyzed and removed to enhance the performance of the isomerization catalyst.

A broad embodiment of the present invention is a process to reduce the nitrogen content of a nitrogen-contaminated light hydrocarbon feed stream, preferably by hydrolysis, in order to provide a nitrogen-depleted hydrocarbon stream to enhance the performance of a nitrogen-sensitive catalyst used in a hydrocarbon-conversion process. Usually a nitrogen contaminant of the feed stream comprises a nitrile, especially one or both of acetonitrile and propionitrile. The feed stream also may be treated for removal of mercaptans and for saturation of highly unsaturated compounds. The process is especially efficacious in treating an olefin-containing stream as feedstock to olefin-etherification or olefin-isomerization processes. In another aspect, the olefin-containing stream is treated for nitrogen removal as feedstock to a complex containing both etherification and olefin-isomerization units.

These as well as other objects and embodiments will become apparent from the detailed description of the invention.

DESCRIPTION Of THE PREFERRED EMBODIMENTS

The present invention encompasses reducing the nitrogen content of a nitrogen-contaminated light hydrocarbon feed stream in a nitrogen-removal zone by conversion, extraction, or adsorption, and preferably by hydrolysis, followed by catalytic processing of the resulting nitrogen-depleted hydrocarbon stream with a nitrogen-sensitive catalyst such as employed in an olefin-etherification or olefin-isomerization process.

The nitrogen-containing light hydrocarbon feed stream comprises hydrocarbons having at least three carbon atoms and distilling at no more than 200° C., and preferably comprises olefins within the $C_3$ to $C_7$ range. The light hydrocarbon distilling feed stream generally contains between 20 and 100 mass % olefins, and more usually between 50 and 80 mass % olefins. The process is especially effective for the processing of streams comprising one or both of butenes and pentenes. In a particularly preferred embodiment, the olefinic portion of the feed stream comprises butenes or pentenes which, following removal of nitrogen contaminants according to the invention, are isomerized skeletally to isoolefins.

The nitrogen content of the light hydrocarbon feed stream may vary widely, broadly up to 1 mass % or more; usually this feed stream will contain between about 1 and 1000 mass parts per million (ppm), and more usually between about 10 and 100 mass ppm, nitrogen. The nitrogen contaminant may comprise a variety of compounds, such as one or more of nitriles, amides, amines, nitrates, cyanide, cyanates, and anilines; the present process is not limited by the nature of the nitrogen contaminant in the feed stream. The nitrogen contaminant often is derived from the cracking of heavier nitrogen-containing feedstocks to obtain the light hydrocarbon feed stream, particularly by catalytic cracking. It is surprising that nitriles are found in butene and pentene concentrates, however, considering the relative boiling points:

| Butenes | −7 to 4° C. |

| -continued | |
| --- | --- |
| Pentenes | 30 to 39° C. |
| Acetonitrile | 82° C. |
| Propionitrile | 97° C. |

Nevertheless nitriles, notably acetonitrile and propionitrile, have been identified as harmful constituents in the catalytic processing of butene- and pentene-containing streams. Propionitrile has been found to be difficult to remove by other methods described in the art such as water washing, and its effective removal is a particular feature of the present invention.

A contaminated feed stream also may contain sulfur compounds, particularly mercaptan sulfur in an amount up to about 1000 mass ppm and perhaps hydrogen sulfide; it is preferred that sulfur compounds be removed to obtain a light hydrocarbon stream as feed to the present process. Oxygenates also may be present in the stream, particulary if all or a portion is derived from an etherification process, and may be removed before, after, or simultaneously with the nitrogen compounds.

At least 90% of the nitrogen contained in the nitrogen contaminant is removed from the light hydrocarbon feed stream by suitable means such as conversion, extraction or adsorption. Optimally, the nitrogen level of a nitrogen-depleted hydrocarbon stream derived from the process is less than about 1.0 mass ppm, especially less than 1 ppm as nitrile. Best results are obtained in a skeletal isomerization process when the nitrogen-depleted hydrocarbon stream contains less than 0.5 ppm nitrogen in the form of acetonitrile, propionitrile, or higher nitrile derivatives, with a level of about 0.1 ppm or less being advantageous in some cases.

Figure 1:
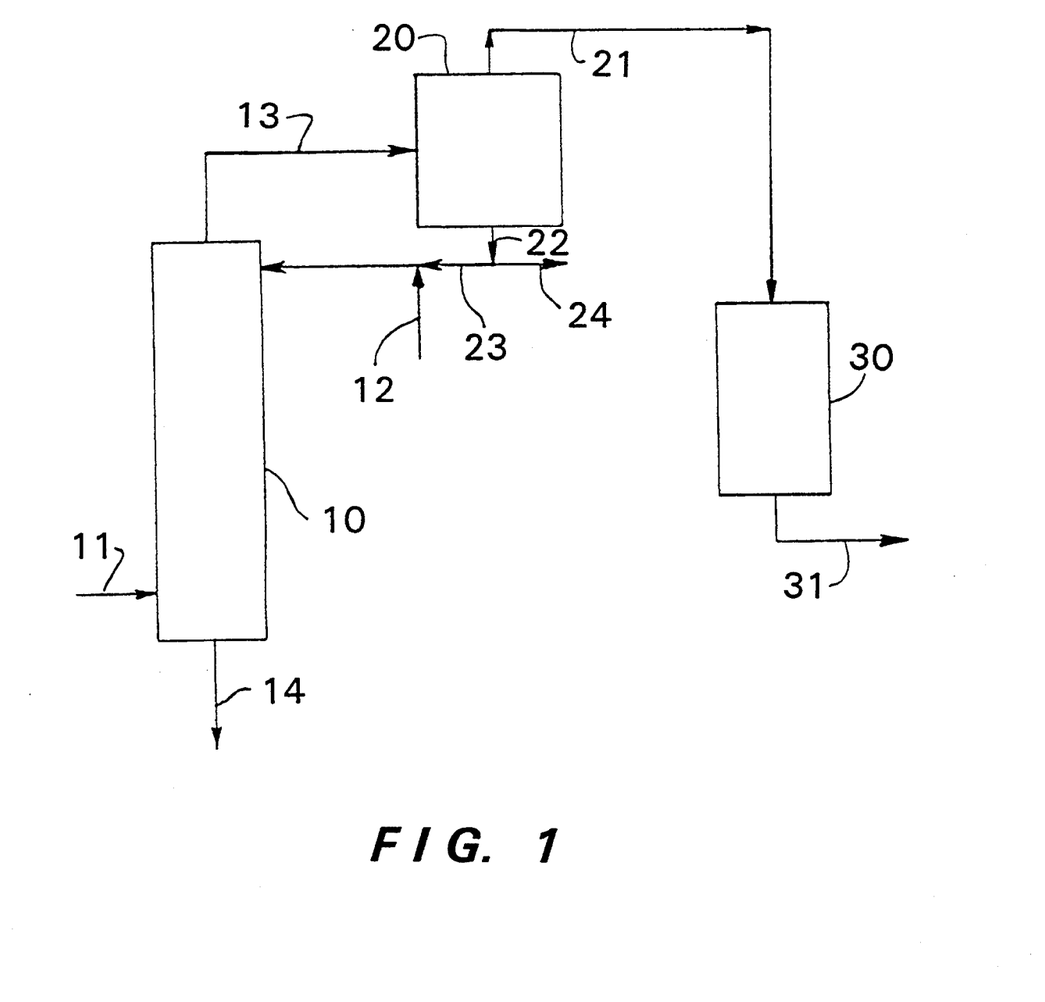
FIG. 1 is a simplified representation of a preferred arrangement of major equipment to effect the process of the invention.

Preferred elements of the nitrogen-removal zone according to the invention are shown in FIG. 1. One preferred embodiment of this zone is a converter 10, which the nitrogen-contaminated light hydrocarbon feed stream enters via line 11 and flows countercurrent to an alkaline solution which enters the converter via line 12; spent alkaline solution leaves the converter. Either or both streams could enter the converter near its upper or lower end and could flow concurrently or countercurrently; in an alternative preferred embodiment, the hydrocarbon stream and alkaline solution flow downward through the converter concurrently. The converter contains means known in the art to enhance the contact between the hydrocarbon and aqueous phases, preferably a particulate bed as discussed hereinbelow. Nitrogen contaminants in the hydrocarbon feed stream are converted to hydrolysis products which are more easily separated from the light hydrocarbon stream, such as ammonia, amides, and carboxylic acids. In the illustrated countercurrent embodiment a stream comprising a hydrocarbon phase, hydrolysis products, and entrained alkaline solution leaves the converter via line 13, and an aqueous phase comprising spent alkaline solution leaves the converter via line 14.

Converter effluent comprising the hydrocarbon phase may pass from the converter to a separator 20 in which a hydrocarbon phase is separated via line 21 from an aqueous phase 22. The hydrolysis products are distributed between the hydrocarbon and aqueous phases according to such factors as solubilities and mass-transfer considerations. A portion of the aqueous phase may be returned to the converter via line 23 to supplement fresh alkaline solution. The net aqueous phase in line 24 is treated for contaminant removal according to means known in the art. Hydrolysis products are removed from the hydrocarbon phase in zone 30 to obtain nitrogen-depleted hydrocarbon stream 31.

Residual products in the hydrocarbon phase may be removed by a variety of known means including water washing, stripping, and adsorption. Water washing is preferred, preferably with the water flowing countercurrent to the hydrocarbon in a column containing flow-distribution media such as trays or packing. The water usually is acidified with a mineral acid to maintain pH at an optimum level below 7.

An alternative means for removal of hydrolysis products is adsorption. Adsorbent requirements are smaller and disposal of products is more facile than if adsorption were used to remove nitrogen compounds from the feed stream. The products may comprise small amounts of amides as well as traces of residual nitriles, but the major portion is ammonia and carboxylic acids. Adsorptive separation would use adsorbents known in the art to remove such contaminants from light hydrocarbon, including zeolitic molecular sieves and resins of the macroporous type. Resins are preferred such as cross-linked polymers of the polystyrene, polyacrylic, polymethacrylic, or phenolformaldehyde type. Spent adsorbent is regenerated in the vapor phase using a contaminant-free stream including one or more of hydrogen, nitrogen, fuel gas, natural gas, and clean light hydrocarbons such as propane, butanes, and/or pentanes.

Conversion of nitrogen contaminants in the light hydrocarbon feed stream within the converter of the nitrogen-removal zone may be effected in accordance with the invention in any suitable manner known in the art, including a batch or a continuous process. In a batch process the light hydrocarbon feed stream is introduced into a conversion zone containing an alkaline solution, and the conversion zone preferably is equipped with suitable stirrers or other devices to effect intimate mixing. In a mixed-type process, the conversion zone contains the alkaline solution and the hydrocarbon is passed continuously through and removed usually from the upper portion of the conversion zone. In the preferred continuous process the alkaline solution is passed countercurrently or concurrently with the light hydrocarbon fraction through the conversion zone which contains packing, particles, perforated trays or other means for achieving effective mixing.

Preferably the converter contains a particulate bed, which may comprise any of the well known stable materials which could provide surface area for the hydrolysis reaction. Preferred materials include graphite and the various charcoals produced by the destructive distillation of wood, peat, lignite, nutshells, bones, and other carbonaceous matter, preferably such charcoals as have been heat-treated or chemically treated or both to form a highly porous particle structure, and generally defined as activated carbon or charcoal. Said materials also include the naturally occurring clays and silicates, e.g., diatomaceous earth, fuller's earth, kieselguhr, attapulgus clay, feldspar, montmorillonite, halloysite, kaolin, and the like, zeolitic and molecular sieves generally and also the naturally occurring or synthetically prepared refractory inorganic oxides such as alumina, silica, zirconia, thoria, boria, etc., or combinations thereof like silica-alumina, silica-zirconia, alumina-zirconia, etc. Any particular solid material is selected with regard to its stability under conditions of its intended use. With regard to its intended use in aqueous systems, perhaps the most important property of the adsorbent support is its insolubility as well as complete unreactivity in aqueous systems. Charcoal, and particularly activated charcoal, is preferred in view of its stability under hydrolysis conditions.

Nitrogen contaminants in the light hydrocarbon feed stream are converted using an acidic or alkaline solution. The solution contains one or more of the known mineral acids or metal hydroxides which are effective for hydrolysis of nitrogen compounds. Generally the solution is alkaline, with a pH above 7, and preferably contains an alkali and/or alkaline-earth metal hydroxide, with sodium and potassium hydroxide being particularly preferred. The concentration of hydroxide may be from 0.5 to 50 mass %, with between 1 and 10 mass % being preferred. The mass ratio of the alkaline solution to the light hydrocarbon feed stream depends on the concentration of nitrogen compounds in the stream and on other operating conditions discussed herein and is from 1:500 to 10:1. Preferably the hydrolysis is carried out with hydrocarbons being the principal phase, at a ratio of solution to light hydrocarbon stream of 1:200 to 1:1. The alkaline solution usually is injected into the converter on a continuous basis, although it is within the scope of the invention that the particulate bed is intermittently treated with an alkaline solution followed by conversion of nitrogen compounds in the light hydrocarbon feed stream in the absence of added solution.

Figure 2:
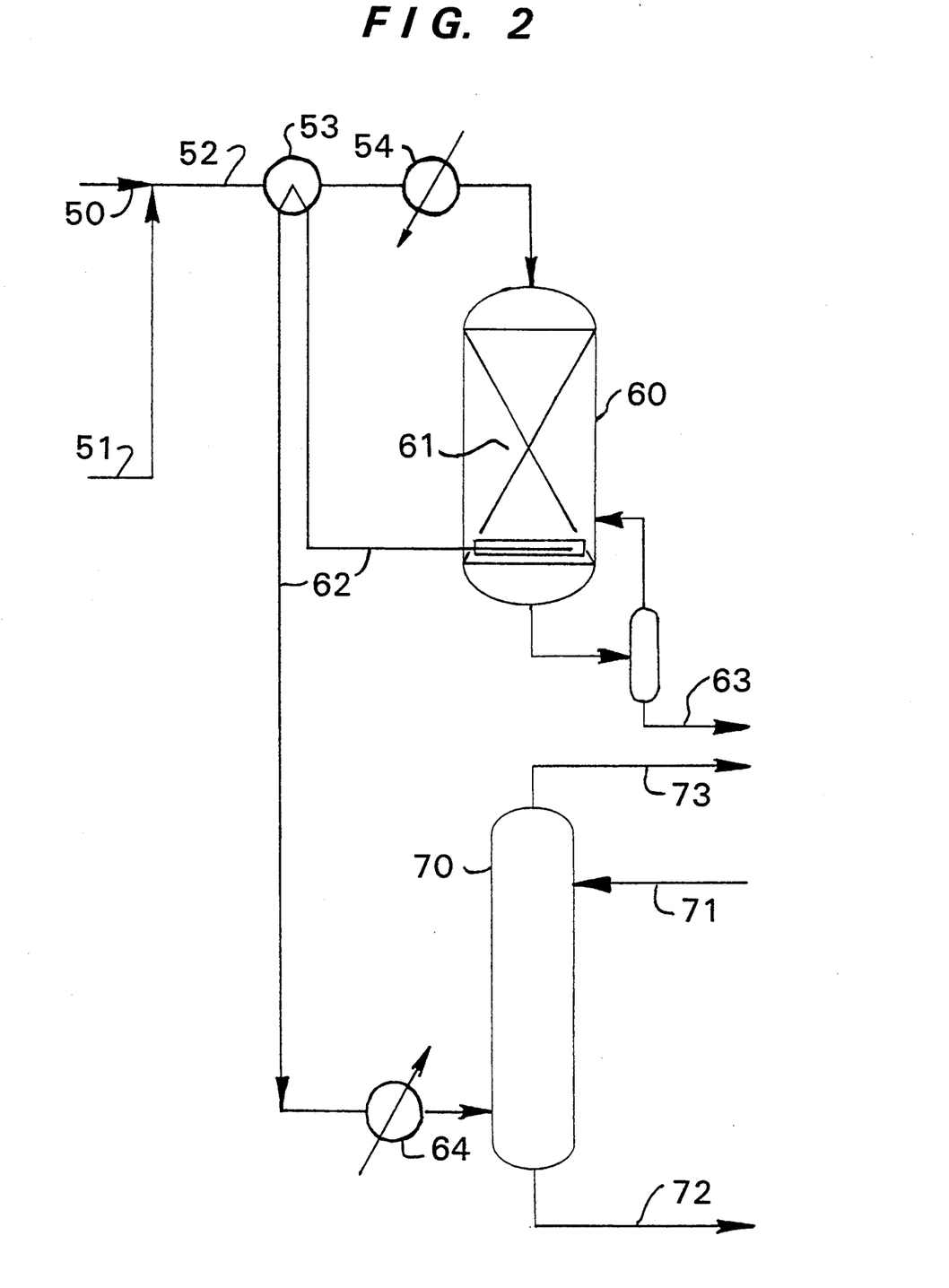
FIG. 2 shows an especially preferred embodiment of the process of the invention.

In an especially preferred embodiment, the ratio of alkaline solution to hydrocarbon is reduced to a level which avoids the need for a solution/hydrocarbon separator and equipment for solution recycle, i.e., a once-through alkaline solution is employed. The ratio of solution to hydrocarbon in this case usually is from about 1:200 to 1:20, and the concentration of alkali metal hydroxide is from about 0.5 to 5 mass % in consideration of the concentrating effect of water dissolution in the hydrocarbon stream. FIG. 2 is a simplified representation of an example of the especially preferred embodiment, showing major vessels and heat-exchange equipment. Light hydrocarbon stream 50 and alkaline solution 51 are combined as stream 52, which passes through heat exchanger 53 and heater 54 to converter 60. Nitriles are converted by hydrolysis over particulate bed 61, usually activated charcoal as discussed hereinabove, to hydrolysis products which are removed near the lower end of the converter in the hydrocarbon stream via line 62. Small amounts of spent alkaline solution are drained via line 63. The hydrocarbon stream and hydrolysis products in line 62 exchange heat with the converter feed in exchanger 53, are cooled in cooler 64, and pass preferably to water-wash column 70. Wash water enters the column via line 71, removing such impurities as ammonia and acids via line 72 with the purified hydrocarbon stream being recovered via line 73.

Hydrolysis conditions comprise a hydrolysis temperature elevated above ambient, as conversion of nitrogen compounds generally is enhanced at higher temperatures, with an effective range, of about 20° to 300° C. and a preferred range of 50° to 175° C. In selecting temperatures within these ranges, considerations known to the skilled routineer of unit metallurgy and thermodynamics are balanced against reaction rates and converter size. Pressure is a less critical variable in conversion of nitrogen compounds; products are maintained in the liquid phase typically at 1 to 100 atmospheres, and more usually 1 to 30 atmospheres. Residence time in the converter varies with the nitrogen content of the feed stream, and is interchangeable to some extent with temperature and to a lesser extent with alkaline-solution strength; a wide range of 1 minute to 10 hours is feasible considering the relationship with other variables, with 0.1 to 2 hours being preferred.

The process of the invention also usually comprises a sulfur-removal zone preceding the nitrogen-removal zone in order to obtain a light hydrocarbon feed stream which is low in mercaptans from a sulfur-containing feed stream. A sulfur-removal zone is required if the light hydrocarbons were derived from a relatively sulfurous crude oil and if prior processing units do not contain sulfur-removal facilities. The sulfur removal zone comprises means for mercaptan removal, generally preceded by facilities for removal of hydrogen sulfide ($H_2S$).

The $H_2S$-removal facilities preferably comprise amine treating as known in the art, using one or a combination of alkanolamines for primary removal of $H_2S$ and partial removal of COS from the sulfur-containing feed stream. The sulfur-containing stream generally contains from about 1 to 5000 ppm sulfur as $H_2S$ and COS, and the sulfur content optimally is reduced by 90 to 95% or more. Operating conditions include temperatures from about 15° to 60° C. and pressures of atmospheric to 35 atmospheres.

The sulfur-containing feed stream, optionally after amine treating, passes to a mercaptan-removal zone in which an alkaline scrubbing solution is utilized to absorb alkaline mercaptans from the feed stream. The alkaline scrubbing solution comprises one or more of aqueous NaOH, KOH, and $NH_4OH$ and a catalyst which preferably is a metal chelate. The mercaptan-containing alkaline solution from the scrubber is contacted with oxygen, preferably in air, to convert mercaptans principally to disulfides in the presence of the catalyst. The disulfides are decanted from the alkaline solution, which then is returned to mercaptan absorption. The temperature in the absorber is between about 10° and 80° C., and the pressure is between about 7 and 250 atmospheres to maintain the alkaline solution in the liquid phase. Mercaptan removal yields a light hydrocarbon stream containing less than 10 mass ppm, and optimally less than 5 ppm, mercaptan sulfur.

The light hydrocarbon feed stream may contain from 0.1 to 5 mass % of highly unsaturated hydrocarbons. Highly unsaturated hydrocarbons include acetylenes and dienes, often formed in high-temperature cracking reactions. When treating the feed stream for subsequent processing in a catalytic olefin isomerization process, a significant concentration of acetylenes and dienes may require higher operating temperatures with correspondingly less favorable equilibrium isomer distribution and also may reduce catalyst life. It is believed that the acetylenes and dienes may form polymer or gum in an isomerization operation, resulting in fouling or coking of the catalyst. In any event, selective reduction of the acetylenes and dienes in a stabilization zone to obtain a stabilized hydrocarbon stream has been found to be advantageous for subsequent catalytic processing. Clay treating by contacting the feed stream with a clay comprising principally amorphous combinations of silica and alumina is one means of removing highly unsaturated hydrocarbons from the feed stream. Other means known in the art of removing highly unsaturated hydrocarbons from the feed stream may be employed, such as the adsorption of diolefins from a mixture also containing monoolefins as taught in U.S. Pat. No. 3,596,436 which is incorporated herein by reference thereto. The stabilization zone may be located before or after the nitrogen-removal zone, but optimally the light hydrocarbon feed stream is processed in the stabilization zone before nitrogen removal.

Preferably, highly unsaturated hydrocarbons are removed from the feed by selective hydrogenation in the stabilization zone. This alternative features the advantage of forming valuable olefins rather than polymer from the acetylenes and dienes, but generally is more costly than clay treating. U.S. Pat. No. 3,470,085 teaches an applicable method for removing diolefins from gasoline by selective hydrogenation, and is incorporated herein by reference thereto. Suitable operating conditions in the stabilization zone include a temperature of from about 20° to 250° C., a pressure of from about 5 atmospheres to 80 atmospheres, and a liquid hourly space velocity of from about 1 to 20. Hydrogen is supplied to the process in an amount sufficient at least to convert diolefins and acetylenes in the feed stream to olefins. A selective-hydrogenation catalyst preferably comprises one or more metals selected from Groups VIB (6) and VIII (8-10) on a refractory inorganic support. One or more of the platinum-group metals, especially palladium and platinum, are highly preferred, and nickel is an alternative metallic component of the catalyst. Alumina is an especially preferred support material.

As mentioned hereinabove, nitrogen removal is particularly advantageous in conjunction with the skeletal isomerization of butenes and/or pentenes in a light hydrocarbon stream. The nitrogen-depleted hydrocarbon stream is contacted with a catalyst containing at least one molecular sieve, preferably a medium-pore molecular sieve having a pore diameter of from about 6 to 8 Å, in an isomerization zone. The molecular sieve may comprise a zeolitic sieve but preferably comprises one or more non-zeolitic molecular sieves, especially the silicoaluminophosphate molecular sieves described in U.S. Pat. No. 4,440,871. Contacting may be effected using the catalyst in a fixed-bed system, a moving-bed system, an ebullated-bed system, a fluidized-bed system, or in a batch-type operation. The isomerization zone may comprise one reactor or separate reactors with suitable means therebetween to ensure that the desired isomerization temperature is maintained at the entrance to each reactor. The reactants may contact the catalyst in the liquid phase, a mixed vapor-liquid phase or a vapor phase in either an upward, downward, or radial-flow manner to produce an isomerization product. The isomerization product contains at least one isomer, preferably a tertiary olefin, in greater concentration than in the hydrocarbon feed stream.

The hydrocarbon stream may contact the catalyst in the absence of hydrogen or in presence of hydrogen in a molar ratio to charge stock of from about 0.01 to 5. Isomerization conditions include reaction temperatures generally in the range of about 50° to 750° C., and preferably between 200° to 600° C. Operating pressures usually will range from about atmospheric to 50 atmospheres. The amount of catalyst in the reactors will provide an overall weight hourly space velocity of from about 0.5 to 100 $hr^{-1}$, and preferably from about 1 to 40 $hr^{-1}$. Further details of the isomerization step are disclosed in U.S. Pat. No. 5,132,484, incorporated herein by reference thereto.

Figure 3:
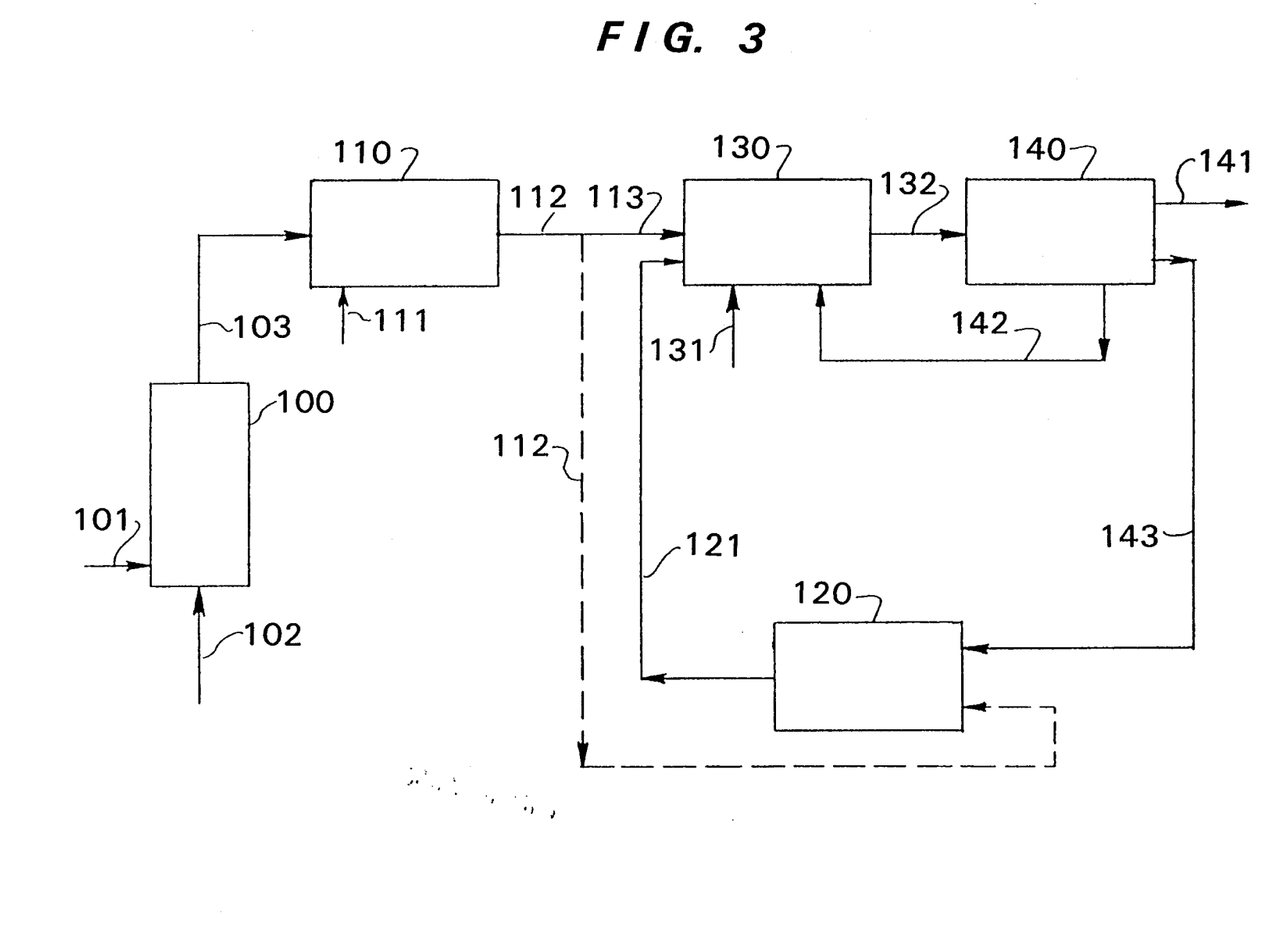
FIG. 3 shows possible alternative positionings of the process of the invention in a complex to isomerize olefins and produce ethers from the isomerized olefins.

Optionally, the nitrogen-removal and isomerization zones are contained within a process combination to produce ether from a light hydrocarbon feed stream as illustrated in FIG. 3. The light hydrocarbon stream first may be subjected to selective hydrogenation, as described hereinabove, to saturate diolefins and acetylenes. This saturation is effected in stabilization zone 100, to which the light hydrocarbon stream 101 is charged, along with a hydrogen-containing stream 102, to yield a product stream 103 which also comprises the feed stream to nitrogen removal. The light hydrocarbon feed stream enters the nitrogen-removal zone 110 and contacts an alkaline solution which enters the zone via line 111. The converter in the nitrogen-removal zone includes separation facilities to remove reactants from the hydrocarbons as described hereinabove and to produce the nitrogen-depleted hydrocarbon stream which leaves the nitrogen-removal zone via line 112.

The product from the nitrogen-removal zone may be the feed stream to a isomerization zone as described hereinabove or to an etherification zone. The former alternative is shown as broken line 114 to isomerization zone 120, producing a product rich in tertiary olefins which is sent via line 121 to etherification zone 130. More usually, when the feed stream contains a substantial concentration of tertiary olefins which can beneficially be etherified, the product from the nitrogen-removal zone 110 passes via line 113 directly to etherification zone 130.

In the etherification zone 130, olefins are combined with one or more monohydroxy alcohols via line 131 to obtain an ether compound having a higher boiling point than the olefin precursor. In order to obtain complete conversion, an excess of the alcohol is usually present in the etherification zone. Methyl tertiary-butyl ether (MTBE) is widely produced from isobutene and methanol, and other useful ethers include ethyl tertiary butyl ether (ETBE), methyl tertiary amyl ether (TAME) and ethyl tertiary amyl ether (TAEE).

The preferred form of the etherification zone is similar to that described in U.S. Pat. No. 4,219,678 wherein isobutene, methanol and a recycle stream containing recovered excess alcohol are passed into the etherification zone and contacted at etherification conditions with an acidic etherification catalyst to produce an effluent containing MTBE. Processes operating with vapor, liquid or mixed-phase conditions may be suitably employed in this invention. The preferred etherification process uses liquid-phase etherification conditions, including a superatmospheric pressure sufficient to maintain the reactants in liquid phase but no more than about 50 atmospheres and an operating temperature between about 30° C. and 100° C. The use of a sulfonated solid resin catalyst is preferred, such as the reaction products of phenolformaldehyde resins and sulfuric acid and sulfonated polystyrene resins including those cross-linked with divinylbenzene. Other suitable catalysts include mineral acids such as sulfuric acid, boron trifluoride, phosphoric acid on kieselguhr, phosphorus-modified zeolites, and heteropoly acids. Further information on suitable etherification catalysts may be obtained by reference to U.S. Pat. Nos. 2,480,940, 2,922,822, and 4,270,929.

An effluent passes via line 132 from the etherification reactor section to a separation section 140 for the recovery of ether product via line 141, preferably by fractional distillation with ether being taken as bottoms product; this product generally is suitable for gasoline blending but may be purified further, e.g., by azeotropic distillation. The overhead from distillation containing unreacted hydrocarbons is passed through a methanol recovery zone for the recovery of methanol via line 142, preferably by water wash and fractionation, with return of the methanol to the etherification zone 130. Heavier oxygenate compounds are removed by passing the stream of unreacted hydrocarbons through a separate oxygenate recovery unit. This hydrocarbon raffinate, after oxygenate removal, is a suitable feed via line 143 for isomerization in zone 120 as described above to produce tertiary olefins by skeletal isomerization. The isomerization product preferably is sent via line 121 to the etherification zone 130, supplementing etherification feed 113 to obtain additional ether product. Alternatively, the isomerization product 121 could be sent to a separate etherification zone if zone 130 has insufficient capacity or differences in tertiary-olefin content would favor separate etherification.

Other embodiments and variants encompassed by and within the spirit of the present invention as claimed will be apparent to the skilled routineer. Examples follow which illustrate certain specific embodiments, and these particularly should not be construed to limit the scope of the invention as set forth in the claims.

Example I

A commercial light hydrocarbon stream from fluid catalytic cracking was analyzed to ascertain the level of trace contaminants present in the stream. The light hydrocarbons comprised principally pentenes (41 mass %) and pentanes (42 mass %), along with small amounts of $C_4$ and $C_{6+}$ hydrocarbons. Trace nitrogen levels were analyzed as follows:

| Contaminant | Level, mass ppm |
| --- | --- |
| Total nitrogen | 22 |
| Nitrogen as acetonitrile | 7 |
| Nitrogen as propionitrile | 14 |

Although the presence of traces of nitrogen was expected, the significant concentration of nitriles was not; the boiling point of nitriles is well above that of the light hydrocarbons in the stream as shown hereinabove.

Example II

The effect of nitrile contamination of the feed on isomerization of olefins was demonstrated in a pilot-plant test. The hydrocarbon feed stream was a mixture of 1-pentene and n-pentane in a molar ratio of 1:1.6, respectively. The test was carried out over a period of about 470 hours at a pressure of 18 atmospheres, temperature of 280° C., hydrogen/hydrocarbon mol ratio of 8, and a liquid hourly space velocity of 9 $hr^{-1}$ with respect to the silica-bound SAPO-11 catalyst used to isomerize the 1-pentene.

Figure 4:
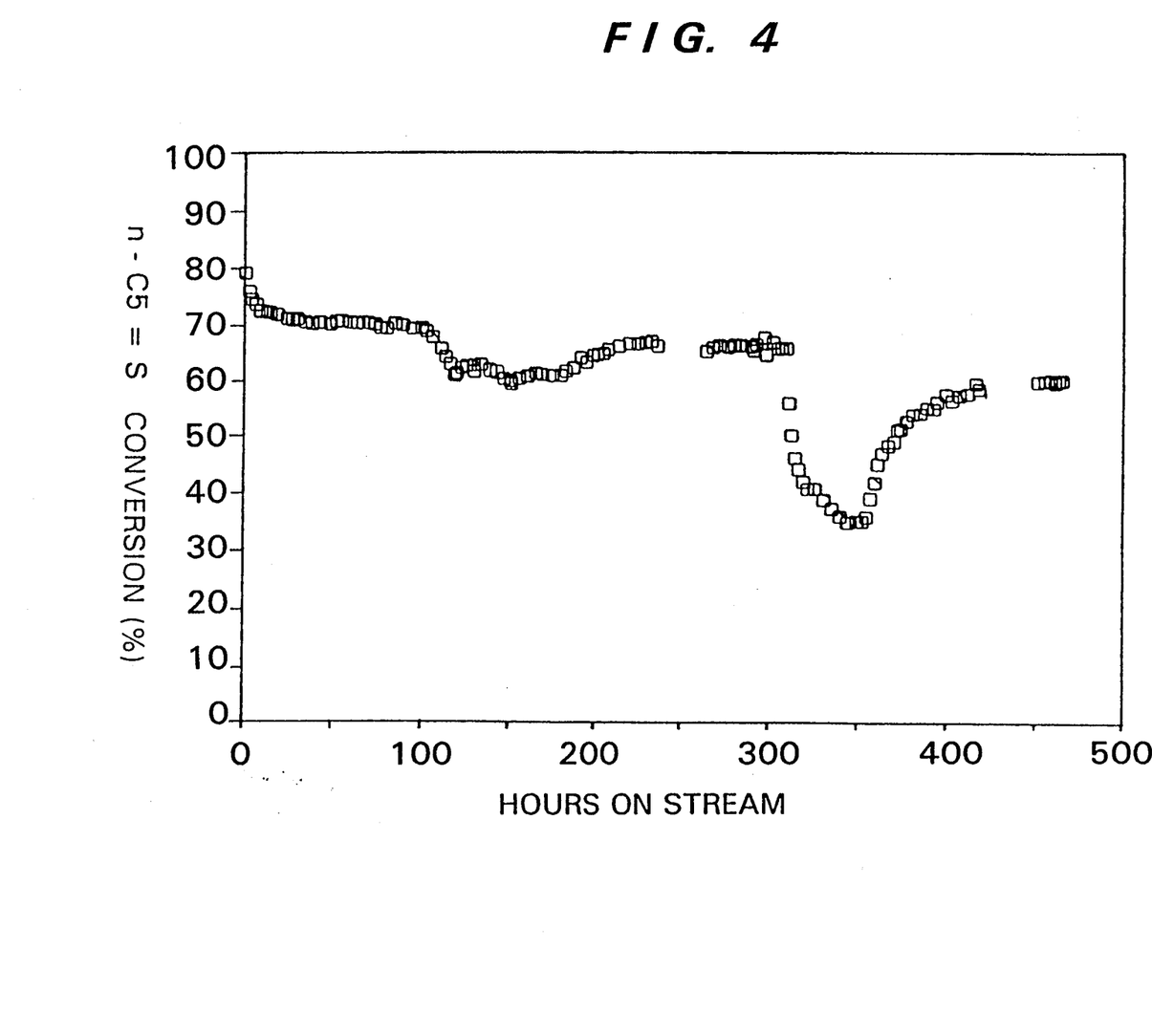
FIG. 4 shows the effect of nitriles on conversion in a pentene-isomerization process.

Propionitrile was present in a concentration of about 11 mass ppm nitrogen starting 70 hours into the test, but was substantially removed in a molecular-sieve bed preceding the catalyst. At about 105 hours on stream, propionitrile broke through the molecular-sieve guard bed and caused a rapid loss in pentene conversion. Pure pentene-pentane feed was introduced to the plant at about 120 hours on stream, and the nitrogen contaminant was flushed from the plant over a period of about 200 hours. At about 310 hours into the run, the molecular-sieve bed was bypassed and propionitrile-contaminated feed (9 mass ppm nitrogen) was introduced to the plant with a resulting rapid drop in pentene conversion. At about 360 hours, pure pentene/pentane feed (<0.4 mass ppm nitrogen as propionitrile) was restored and conversion gradually recovered. The plot of conversion in relation to time on stream is shown as FIG. 4.

Example III

A second pilot-plant test was performed in order to determine the effect of nitrogen removal on an olefin-isomerization process. The feedstock was derived from a commercial fluid catalytic cracking unit, and comprised principally $C_5$ hydrocarbon with a molar ratio of n-pentene: i-pentene: pentanes respectively of about 0.45:0.55:1.6. The feedstock contained 3.3 mass ppm nitrogen as propionitrile. After a line-out period using a synthetic feed, the isomerization test on commercially derived feed was carried out over a period of about 50 hours at a pressure of 18 atmospheres, a temperature of 327° C., hydrogen/hydrocarbon mol ratio of 3.1, and a liquid hourly space velocity of 23 $hr^{-1}$ with respect to the silica-bound SAPO-11 catalyst used to isomerize the pentenes.

Figure 5:
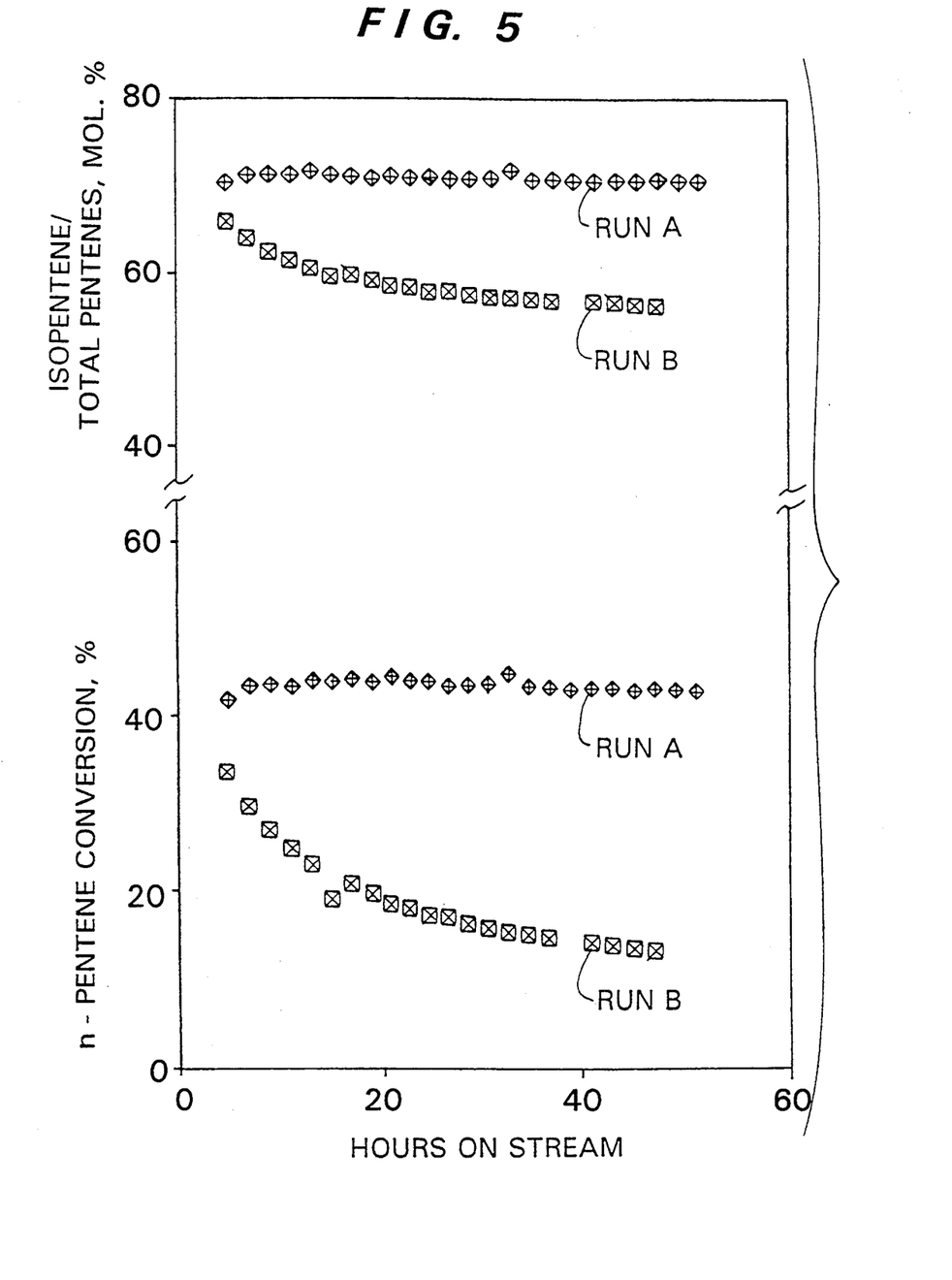
FIG. 5 compares conversion and the degree of isomerization in an olefin-isomerization process with and without nitrogen removal from a commercial pentene-containing feed.

Two runs were carried out to demonstrate the effect of nitrogen removal. In Run A, nitrogen removal from the feedstock was effected using successive beds of sulfonic acid resin and Linde 3A molecular sieves; the nitrogen content of the treated feedstock to isomerization was less than 0.1 mass ppm. In control Run B, the feedstock was not treated and the nitrogen content thus was 3.3 mass ppm. Nitrogen removal effected significant improvements in conversion and isopentene yield, as shown in FIG. 5.

Example IV

Removal of nitrogen from a light hydrocarbon feed stream according to the present invention was demonstrated in a pilot plant. The light hydrocarbon was an isopentane stream containing from 48 to 53 mass ppm propionitrile. Hydrolysis was effected by mixing the hydrocarbon stream at a 5:1 ratio with an alkaline solution containing 7 mass % NaOH in a static mixer and passing the mixture at a pressure of about 14 atmospheres to a downflow contactor. The contactor contained Darko MRX carbon (10–30 mesh, 0.383 g/cc ABD, 0.667 g/cc piece density) obtained from Norit. Temperature in the contactor was varied between 70° and 100° C., and contact time of the hydrocarbon and carbon was varied between 1.4 and 2.9 hours as indicated below. The combined effluent from the contactor was passed to a separator, in which the aqueous phase was separated from the hydrocarbon phase. The latter was analyzed for trace nitrogen components, using a gas-liquid chromatograph, with the following results:

| Temperature, °C. | Contact Time, hr | Nitrile, mass ppm |
|---|---|---|
| 70 | 1.4 | 39 |
| 85 | 1.4 | 17 |
| 100 | 1.4 | 4 |
| 100 | 2.9 | <0.5 |

We claim:

1. A process for the isomerization of olefins contained in a nitrile contaminated light hydrocarbon feed stream comprising the steps of:
 (a) reducing the content of a nitrile contaminant in the nitrile contaminated feed stream by at least 90% in a nitrogen-removal zone by hydrolyzing the nitrile contaminant at hydrolysis conditions in the presence of an alkaline solution and recovering a nitrile depleted hydrocarbon stream; and,
 (b) contacting the nitrile depleted hydrocarbon stream in an isomerization zone at isomerization conditions with a catalyst containing at least one medium-pore molecular sieve to provide an isomerization product containing at least one branched-chain olefin isomer in greater concentration than in the feedstock.

2. The process of claim 1 wherein the nitrile contaminant comprises one or both of acetonitrile and propionitrile.

3. The process of claim 1 wherein the nitrile-contaminated light hydrocarbon stream is derived from a fluid catalytic cracking unit.

4. The process of claim 1 wherein the hydrocarbon stream comprises pentenes.

5. The process of claim 1 wherein the nitrile content of the nitrile depleted hydrocarbon stream is less than 1 mass ppm.

6. The process of claim 1 wherein the alkaline solution contains an alkali or alkaline earth metal hydroxide.

7. The process of claim 6 wherein the hydroxide comprises one or both of sodium hydroxide and potassium hydroxide.

8. The process of claim 1 wherein a hydrocarbon phase from hydrolysis is water-washed to remove contaminants remaining after hydrolysis of the nitrile contaminant and obtain a nitrile depleted hydrocarbon stream.

9. The process of claim 1 wherein a hydrocarbon phase from hydrolysis is contacted with a selective adsorbent to remove contaminants remaining after hydrolysis of the nitrile contaminant and obtain a nitrile-depleted hydrocarbon stream.

10. The process of claim 1 wherein the hydrolysis conditions comprise a temperature of from about 20° to 300° C., a pressure of from about atmospheric to 100 atmospheres, and a contact time of from about 1 minute to 10 hours.

11. The process of claim 1 further comprising contacting the light hydrocarbon stream in a stabilization zone to selectively reduce the content of diolefinic and acetylenic hydrocarbons and obtain a stabilized hydrocarbon stream.

12. A process for the isomerization and etherification of olefins contained in a nitrile-contaminated light hydrocarbon feed stream comprising the steps of:
 (a) reducing the content of a nitrile contaminant in the nitrile-contaminated feed stream by at least 90% in a nitrile-removal zone by hydrolyzing the nitrile contaminant at hydrolysis conditions in the presence of an alkaline solution and recovering a nitrile depleted hydrocarbon stream;
 (b) contacting the nitrile depleted hydrocarbon stream with an alcohol in an etherification zone at etherification conditions to obtain an ether product and a hydrocarbon raffinate: and,
 (c) contacting the hydrocarbon raffinate in an isomerization zone at isomerization conditions with a catalyst containing at least one medium-pore molecular sieve to provide an isomerization product containing at least one branched chain olefin isomer in greater concentration than in the feedstock.

13. The process of claim 12 further comprising contacting the isomerization product in the etherification zone with an alcohol to obtain an additional ether product.

14. The process of claim 12 further comprising contacting the isomerization product in a separate etherification zone with an alcohol to obtain an additional ether product.

* * * * *

UNITED STATES PATENT AND TRADEMARK OFFICE
CERTIFICATE OF CORRECTION

PATENT NO. : 5,414,183
DATED : May 9, 1995
INVENTOR(S) : Abrevaya et al.

It is certified that error appears in the above-indentified patent and that said Letters Patent is hereby corrected as shown below:

In Column 11, line 61:   insert a dash between the words "nitrile" and "contaminated"

line 64:   insert a dash between the words "nitrile" and "contaminated"

line 65:   Change "nitrogen" to --nitrile--.

line 68:   insert a dash between the words "nitrile" and "depleted".

In Column 12, line 1:   insert a dash between the words "nitrile" and "depleted".

Signed and Sealed this

Eighteenth Day of July, 1995

Attest:

BRUCE LEHMAN

Attesting Officer     Commissioner of Patents and Trademarks